United States Patent [19]
Akima et al.

[11] Patent Number: 5,872,109
[45] Date of Patent: Feb. 16, 1999

[54] ANTI-INFLAMMATORY AGENT

[75] Inventors: Kazuo Akima, Yokohama, Japan; Peter A. Ward, Ann Arbor, Mich.; Masayuki Miyasaka, Suita; Yasuo Suzuki, Shizuoka, both of Japan

[73] Assignee: Shiseido Company, Ltd., Japan

[21] Appl. No.: 722,131
[22] PCT Filed: Feb. 6, 1996
[86] PCT No.: PCT/JP96/00239
§ 371 Date: Oct. 4, 1996
§ 102(e) Date: Oct. 4, 1996
[87] PCT Pub. No.: WO96/24362
PCT Pub. Date: Aug. 15, 1996

[30] Foreign Application Priority Data

Feb. 7, 1995 [JP] Japan ..................................... 7-41407

[51] Int. Cl.$^6$ .............................. A01N 43/04; C07H 5/04
[52] U.S. Cl. ................................. 514/54; 514/56; 536/21; 536/55.1
[58] Field of Search ....................... 536/55.1, 21; 514/54, 514/56

[56] References Cited

U.S. PATENT DOCUMENTS

| 4,840,941 | 6/1989 | Ueno et al. ................................. 514/59 |
| 5,013,724 | 5/1991 | Petitou et al. ............................. 514/54 |

FOREIGN PATENT DOCUMENTS

| 0 208 623 | 1/1987 | European Pat. Off. . |
| 0 214 879 | 3/1987 | European Pat. Off. . |
| 0 717 995 | 6/1996 | European Pat. Off. . |
| 52-35710 | 9/1977 | Japan . |
| 62-201825 | 9/1987 | Japan . |
| 2-7577 | 2/1990 | Japan . |
| 6-107550 | 4/1994 | Japan . |
| 8-92103 | 4/1996 | Japan . |
| 88/07060 | 9/1988 | WIPO . |
| 89/05646 | 6/1989 | WIPO ..................................... 514/54 |
| 92/18545 | 10/1992 | WIPO . |
| 94/18989 | 9/1994 | WIPO . |
| 94/26759 | 11/1994 | WIPO . |
| 95/25751 | 9/1995 | WIPO . |

OTHER PUBLICATIONS

Medline, 89/346421, Modig, "Increased hyaluronic acid production", (1989).

Chemical abstract, vol. 83, No. 188237, Schupp et al, "Response of the formation of collagen fibrils in vito to antiinflammatory agents"(1975).

Chemical abstract, vol. 111, No. 131848, Willershausen et al, Influence of elevated glucose concentrations on the metabolism of gingival fibroblasts, (1989).

T. Tamatani et al., "Characterization of rat LECAM–1 (L–selectin) by the use of monoclonal antibodies and evidence for the presence of soluble LECAM–1 in rat sera", Eur. J. Immunol., vol. 23, pp. 2181–2188, 1993.

L. Stoolman et al., "Phosphomannosyl receptors may participate in the adhesive interaction between lymphocytes and high endothelial venules", J. Cell Biol., vol. 99, pp. 1535–1540, 1984.

T. Yednock et al., "Phosphomannosyl–derivatized beads detect a receptor involved in lymphocyte homing", J. Cell Biol., vol. 104, pp. 713–723, 1987.

L. Stoolman et al., "Homing receptors on human and rodent lymphocytes—evidence for a conserved carbohydrate–binding specificity", Blood, vol. 70, pp. 1842–1850, 1987.

Y. Imai et al., "Direct demonstration of the lactin activity of $gp90^{mel}$, a lymphoctye homing receptor", J. Cell Biol., vol. 111, pp. 1225–1232, 1990.

M. Mulligan et al., "Role of $\beta_1$, $\beta_2$ integrins and ICAM–1 in lung injury after deposition of IgG and IgA immune complexes[1]", J. Immunol., vol. 150, pp. 2407–2417, 1993.

K. Kawasaki et al. "Antibodies against intercellular adhesion molecule–1 and lymphocyte function–associated antigen–1 prevent glomerular injury in rat experimental crescentic glomerulonephritis[1]", J. Immunol., vol. 150, pp. 1074–1083, 1993.

M. Mulligan et al., "Protective effects of oligosaccharides in P–selectin–dependent lung injury", Letters To Nature, vol. 364, 149–151, 1993.

Primary Examiner—C. Warren Ivy
Assistant Examiner—Raymond Covington
Attorney, Agent, or Firm—Wenderoth, Lind & Ponack

[57] ABSTRACT

Use of a polysaccharide selected from the group consisting of sulfated acid mucopolysaccharides and sulfated dextrans, and physiologically acceptable salts thereof for prophylaxis or treatment of inflammations, particularly an adult respiratory distress syndrome (ARDS), ischemic heart diseases, ischemic cerebral diseases, chronic articular rheumatism, atopic dermatitis, and infiltration after organ implantation.

10 Claims, No Drawings

ANTI-INFLAMMATORY AGENT

TECHNICAL FIELD

This invention relates to an anti-inflammatory agent or the like having a new action mechanism. More specifically, this invention relates to a use for treatment or prophylaxis of inflammation, etc. of a sulfated acid mucopolysaccharide or sulfated dextran screened based on a new action mechanism.

BACKGROUND OF THE INVENTION

Nowadays, corticoids or various non-steroidal anti-inflammatory agents are clinically widely used for the purpose of preventing complications due to inflammation. However, since although corticoids exhibit a strong anti-inflammatory action, grave side effects such as induction of infectious diseases accompany the action, they cannot serially be administered, and non-steroidal anti-inflammatory agents have only weak efficacy in general. Therefore, it is still needed to develop anti-inflammatory agents exhibiting almost no side effect and yet having sufficient efficacy.

Incidentally, in the screening systems by which anti-inflammatory agents as mentioned above had been developed, anti-prostaglandin actions (e.g., phospholipase A2 inhibition, cyclooxygenase inhibition, lipoxygenase inhibition) had generally been used as a measure. On the other hand, in this invention, the present inventors intend to solve the above problems from the viewpoint that an utterly novel-type of anti-inflammatory agents may probably be developed by utilizing a screening system constructed based on the findings on induction of inflammation being clarified recently (i.e., a screening system using as a measure inhibition of influx of neutrophils, more specifically, selectin-mediated inhibition of adhesion of neutrophils to vascular endothelial cells).

In order to clarify the sense of the screening system used in the invention, the findings of its background are outlined below. For example, inflammation is speculated to be induced by molecules promoting adhesive interactions between leukocytes and vascular endothelial cells, and it has also come to be clarified that certain adhesion promoting molecules play an important role for promotion of the adhesive interaction. Further, it is also revealed that adhesion promoting molecules exist in both leukocytes and activated vascular endothelial cells (blood vessel at the inflammation site), and interactions between these adhesion promoting molecules are the first indispensable stage for influx of leukocytes to the inflammatory site. These adhesion promoting molecules are molecules found in both leukocytes and activated vascular endothelial cells, and selectin family and integrin family are the most important as the molecules.

On the other hand, it is also reported to use, for control of the above interactions, monoclonal antibodies (Eur. J. Immunol., 23, 2181–2188, 1993), peptides and further certain oligosaccharides (J. Cell Biol., 99, 1535, 1984; Tednok et al., J. Cell Biol., 104, 713, 1987; Blood, 70, 1842, 1987). Further, although leukocytes adhere to endothelial cells in the lymph node through the above action of selectin, it is clarified that this response is inhibited by certain sulfate radical-containing compounds (J. Cell Biol., 111, 1225, 1990). It is still further reported that inflammatory response can be inhibited in various laboratory animal model by inhibiting the above adhesive interactions (J. Immunol., 150, 2407; J. Immunol., 150, 1074 etc.).

However, it is not clarified whether or not these monoclonal antibodies, peptides, oligosaccharides and sulfate radical-containing compounds can actually be used as anti-inflammatory agents.

The present inventors found that the neutrophil-dependent, oxygen radical-mediated and P-, L- or E-selectin-dependent inflammation model obtained by intravenous administration to rats of cobra venom factor (hereafter, sometimes abbreviated as "CVF"), recently proposed in M. S. Mulligan et al., Nature, 364, 149–151, 1993, is an excellent screening method for anti-inflammatory agents. More specifically, they found that specific polysaccharides such as sulfated hyaluronic acid screened using the above laboratory animal model exhibit excellent anti-inflammatory actions, and can, particularly, be used for prophylaxis or treatment of adult respiratory distress syndrome (ARDS). This syndrome is such a grave disease that 50 to 70% of patients suffering therefrom die (Igaku no Ayumi, 168 (no. 6), 626–631). It was further found that since substances screened using the above laboratory animal model inhibit the influx of neutrophils to the vascular endothelial adhesion tissue mediated by selectin, these substances show efficacy not only on ARDS but widely on general inflammations, and show efficacy further on ischemic heart diseases, ischemic cerebral diseases, chronic articular rheumatism, atopic dermatitis and infiltration after organ implantation.

In this connection, although it is suggested that sulfates of various saccharides including sulfated hyaluronic acid is usable for treatment of diseases caused by human immunodeficiency viruses (Japanese Patent Publication No. 7577/1990), it has not hitherto been disclosed in technical literatures that these saccharides can be used as anti-inflammatory agents.

DISCLOSURE OF THE INVENTION

Thus, according to the invention, an anti-inflammatory agent is provided comprising an effective amount of a polysaccharide selected from the group consisting of sulfated acid mucopolysaccharides and sulfated dextrans, and physiologically acceptable salts thereof, and pharmaceutical auxiliaries.

Further, according to the invention of another embodiment, there is provided a method for treating an inflammation using the above polysaccharide. More specifically, according to the invention, there is provided a method for treating a disease selected from the group consisting of an adult respiratory distress syndrome (ARDS), ischemic heart diseases, ischemic cerebral diseases, chronic articular rheumatism, atopic dermatitis, and infiltration after organ implantation, which comprises using a polysaccharide selected from the group consisting of sulfated acid mucopolysaccharides and sulfated dextrans, and physiologically acceptable salts thereof.

Further, according to the invention of still another embodiment, there is provided use of a polysaccharide selected from the group consisting of sulfated acid mucopolysaccharides and sulfated dextrans, and physiologically acceptable salts thereof for preparing a medicament for treating inflammation, and a disease selected from the group consisting of ARDS, ischemic heart diseases, ischemic cerebral diseases, chronic articular rheumatism, atopic dermatitis, and infiltration after organ implantation.

DETAILED DESCRIPTION OF INVENTION

The sulfated acid mucopolysaccharide used in the invention means a long-chain polysaccharide having a repeating unit of a disaccharide composed by a hexosamine (in many cases, N-acetylated glucosamine or N-acetylated galactosamine) and an uronic acid (D-glucuronic acid or L-iduronic acid) and having sulfate radicals. Since some natural acid mucopolysaccharides have sulfate radicals, they themselves, and if desired, those further chemically sulfated are included in the sulfated acid mucopolysaccharide of the invention. Further, acid mucopolysaccharide having no sulfate radical come to be usable in the invention by chemically introducing sulfate radicals.

Specific examples of these acid mucopolysaccharides are chondroitin 4-sulfate and 6-sulfate, dermatan sulfate, heparan sulfate (also referred to as heparitin sulfate) heparin sulfate and keratan sulfate as those having sulfate radicals, and hyaluronic acid and chondroitin as those having no sulfate radicals.

Further, sulfated dextran can also be used in the invention. Those sulfated acid mucopolysaccharides and sulfated dextran include partial sulfate esters which are known to have a heparin-like anticoagulant action and are used clinically.

Among the above various sulfated saccharides, sulfated hyaluronic acid is particularly preferable from the viewpoint of availability of its raw material and efficacy. Sulfated hyaluronic acid is a compound obtained by sulfating hyaluronic acid (a straight-chain high molecular saccharide formed by alternate bond of β-D-N-acetyglucosamine and β-D-glucuronic acid) derived from comprehensive natural sources, for example connective tissues of mammals, cockscombs of chickens, gastroantral membranes of silkworms, capsules of streptococci, etc. Since although as to hyaluronic acid varience of molecular weight generally exists depending on the kind of sources, ununiformity on structure is not known, hyaluronic acid of any source can be used. However, in view of availability, hyaluronic acid derived from streptococci, although not limited thereto, can conveniently be used. A specific example thereof is hyaluronic acid prepared according to a process as described in Japanese Laid-Open Patent Publication No. 26692/1983. This has, in general, a molecular weight of about 2,000 kDa. Hyaluronic acid is, if desired, adjusted for molecular weight by partial hydrolysis or the like, and when the rapid action of the final product is expected, one having a low molecular weight (hereafter abbreviated as LMWHA) is used for the succeeding sulfation treatment, and when the prolonged action thereof is expected, one having a high molecular weight (hereafter abbreviated as HMWHA) is used therefor.

Although hyaluronic acid can be sulfated according to a process known per se, a process comprising using a sulfuric acid-trimethylamine complex as a sulfating agent is preferable. The use ratio between hyaluronic acid and a sulfating agent can freely be chosen in accordance with the sulfation rate (or sulfur content) of the desired sulfated hyaluronic acid and the reaction conditions. In general, when the reaction is carried out at a temperature of 50° to 60° C. over a period from scores of hours to several days, the amount of the sulfating agent is chosen so as to be about two times by weight that of hyaluronic acid. The thus attained sulfation rate is generally about 50 to 60% of the total hydroxyl groups of hyaluronic acid.

The resultant sulfated hyaluronic acid can be purified according to purification operations conventionally used for various modified polysaccharides. Specific purification operations include steps of concentrating the reaction mixture under reduced pressure, dialyzing the concentrate against water to desalt it, removing trimethylamine by trifluoroacetic acid treatment and freeze-dry the residue.

Other acid mucopolysaccharides can be converted to the corresponding sulfated acid mucopolysaccharides in the same manner as in the above sulfation treatment of hyaluronic acid. Although the optimal values of their molecular weight and sulfation rate vary depending on the kind of the saccharides, a person skilled in the art can readily choose these optimal values through the alter-described efficacy test, etc.

The sulfated acid mucopolysaccharide or sulfated dextran can, if desired, be used in the form of a physiologically acceptable salt obtained by reaction with a hydroxide or carbonate of an alkali metal or an amine.

The above sulfated acid mucopolysaccharide or sulfated dextran or a physiologically acceptable salt can be mixed with pharmaceutical auxiliaries, for example, diluents or excipients used for preparation of usual pharmaceutical preparations to give liquids or suspensions which can then be administered parenterally, e.g. intravenously, intraarterially or intraperitoneally. Pharmaceutical auxiliaries usually used in the liquids include, for example, water, ethyl alcohol, propylene glycol, etc., and those in the suspensions include polyoxyethylenesorbitol and sorbitan esters.

The optimal mixing ratio between the auxiliaries and the sulfated acid mucopolysaccharide or sulfated dextran is not limited because it varies depending on the dosage forms, but when sulfated hyaluronic acid is made into injections, it is convenient for treatment of patients to adjust the concentration of the sulfated hyaluronic acid to 0.01 to 10% by weight/volume, preferably 0.05 to 1% by weight/volume in physiological saline. It is of course possible to prepare a concentrated preparation and make it into an injection as mentioned above immediately before use.

The optimal dose of sulfated hyaluronic acid as an effective ingredient varies depending on the age of patients, the kind and gravity of diseases, and dosage formes and administration routes, but in the case of intravenous injections, it can be 0.01 to 1,000 mg/kg, preferably 0.1 to 10 mg/kg. Nevertheless, since sulfated hyaluronic acid and other sulfated acid mucopolysaccharides and sulfated dextran do not show acute toxicity even at a dose of 2,000 mg/kg or more, they may be used beyond the above dose.

The above-described anti-inflammatory agent of this invention significantly inhibits vascular permeability, hemorrhage accompanying inflammation and myeloperoxidase (MPO) activity on the laboratory animal model caused by administration of cobra venom factor, and therefore can be used widely, as an anti-inflammatory agent, for prophylaxis or treatment particularly of ARDS, ischemic heart diseases, ischemic cerebral diseases, chronic articular rheumatism, atopic dermatitis, and infiltration after organ implantation.

This invention is further detailedly described below by specific examples, but the invention should not be limited thereto.

PREPARATION EXAMPLE 1

High molecular hyaluronic acid (HMWHA; molecular weight 1,300 kDa) (200 mg) and 400 mg of sulfuric acid-trimethylamine complex (Aldrich) were dissolved in 6 ml of dimethylformamide, and the solution was stirred at 50° to 60° C. for one week in an oil bath. The reaction solution was concentrated under reduced pressure using a vacuum pump, the residue was dissolved in water, and the solution was dialyzed against deionized water overnight and freeze-dried. The resultant dry matter was dissolved in 2 mL of water, trifluoroacetic acid (an amount corresponding to 1.5 times the molar quantity of the total hydroxyl groups of HMWHA) was added, and the mixture was stirred at room temperature for one hour. After dialysis, the reaction solution was freeze-dried to give 200 mg of sulfated hyaluronic acid having a sulfation rate of about 60%.

PREPARATION EXAMPLE 2

The same operations as in Example 1 were repeated except that hyaluronic acid having a low molecular weight (LMWHA, molecular weight 40 kDa) was used in place of the high molecular hyaluronic acid. Thus sulfated low molecular weight hyaluronic acid having a sulfation rate of about 50 to 60% was obtained.

Assessment Test for Anti-inflammatory Action (1) Preparation of Inflammation Model Animals and Inflammation Assessment Method Specific pathogen-free, adult (250–350 g) male Long-Evans rats were used. Cobra venom factor (CVF) was isolated from *Naja naja* crude venom by procedures described in Till et al., *J. Clin. Invest.*, 69, 1126–1135, 1982. 20 U/kg body weight of CVF together with an aliquot each of $^{125}$I-BSA (0.5μ Ci) and $^{51}$Cr-rat red blood cells (RBC) were injected intravenously to the rats as a bolus infusion.

Animals were anesthetized with ketamine hydrochloride (100 mg/kg) (Parke Davis and Co. Morris Plains, N.J.) and exsanguinated via the posterior vena cava 30 minutes after infusion of CVF. Negative control animals were similarly treated except that phosphate buffered saline (PBS, pH 7.4) was used in placed of CVF. At the 30 minutes interval the lung vasculature was perfused through the right cardiac ventricle with 10 mL of PBS. The lungs were removed, the vasculature perfused with 10 mL of sterile physiological saline, and the amount of radioactivity remaining within the tissue was assessed with a gamma scintillation counter. The positive control value is a value when the test substance was not administered.

Lung damage was defined by increased lung vascular permeability (as determined by the ratio of $^{125}$I-BSA radio-activity present within lung tissue to the amount of radio-activity present in 1.0 mL of venous blood obtained at the time of death) and by hemorrhage ($^{51}$Cr-RBC radioactivity), which was similarly quantitated as a ratio to blood radioactivity. Protection from lung injury was calculated using the following equation:

$$\text{Protection (\%)} = 100 \times \frac{\text{Test substance value} - \text{Negative control (PBS) value}}{\text{Positive control value} - \text{Negative control (PBS) value}}$$

(2) Tissue Myeloperoxidase (MPO) Activity

To assess MPO activity as a measure of neutrophil influx, known numbers of glycogen-elicited rat peritoneal neutrophils were added to normal rat lungs, the tissue homogenized and extracted, and standard curves produced (see Warren et al., *J. Clin. Invest.*, 84, 1873–1882, 1989). Lung samples were homogenized with a homogenizer (Polytron; Tekmar Co., Cincinati, Ohio), 4×10 seconds at a setting of 4, using 6 mL of homogenization buffer (50 mM phosphate, pH 6.0) and then subjected to centrifugation (3,000 g, 30 minutes) at 4° C. MPO activity in supernatant fluids was assayed by measuring the change in absorbance (460 nm) resulting from decomposition of $H_2O_2$ in the presence of o-dianisidine.

(3) Results

Results obtained when various test substances were intra-venously administered in an amount of each 1 mg/kg immediately before the administration of CVF of the above (1) are shown in the following table.

| Exp. No. | Test substance intravenously infused | Amount | Reduction (%) in lung injury Perme-ability | Hemorr-hage | MPO |
|---|---|---|---|---|---|
| 1. | Sulfated HMWHA | 1 mg | 84 | 63 | 60 (0.001) |
| 2. | Sulfated LMWHA | 1 mg | 62 | 31 | not assayed |
| 3. | Heparin sulfate* | 1 mg | 43 | −6 | not assayed |
| 4. | Sulfated dextran** | 1 mg | 8 | −31 | not assayed |
| 5. | HMWHA (control) | 1 mg | 4 | 0 | 0 |
| 6. | Sialyl-Lews X*** (Comparison) | 1 mg | 35 | 6 | not assayed |

*produced by Wako Pure Chemical Industries, Ltd.
**produced by KOWA COMPANY, LTD.
***see M. S. Mulligan et al., Nature, Vol. 364 (1993) pp. 149–150

As shown above, sulfated polysaccharides of this invention can significantly protect lung injury caused by administration of cobra venom factor (CVF).

PHARMACEUTICAL PREPARATION EXAMPLE

| | |
|---|---|
| Sulfated HMWHA | 1 g |
| Phosphate buffer (PBS) made to be isotonic | 1 L |

Preparation

Sulfated HMWHA is dissolved in sterilized PBS.

INDUSTRIAL APPLICABILITY

This invention provides an anti-inflammatory agent having a different action mechanism from usual anti-inflammatory agents. The anti-inflammatory agent of the invention exhibits a powerful anti-inflammatory action by using as an effective ingredient a sulfated acid mucopolysaccharide or sulfated dextran. The invention also provides a method for treating or preventing inflammations, particularly ARDS, ischemic heart diseases, ischemic cerebral diseases, chronic articular rheumatism, atopic dermatitis and infiltration after organ implantation, wherein a sulfated acid mucopolysaccharide or sulfated dextran is used as an effective ingredient. Thus, the invention has applicability in the pharmaceutical industry.

We claim:

1. An anti-inflammatory agent for the treatment of a disease selected from the group consisting of an adult respiratory distress syndrome (ARDS), ischemic heart diseases, ischemic cerebral diseases, chronic articular rheumatism, atopic dermatitis, and infiltration after organ implantation, comprising an effective amount for the treatment of such disease of a sulfated hyaluronic acid, and physiologically acceptable salts thereof, and pharmaceutical auxiliaries.

2. A method for the treatment of a disease selected from the group consisting of an adult respiratory distress syndrome (ARDS), ischemic heart diseases, ischemic cerebral diseases, chronic articular rheumatism, atopic dermatitis, and infiltration after organ implantation, which comprises administering an effective amount for the treatment of such disease of a sulfated hyaluronic acid to a patient in need of such treatment.

3. The method according to claim 2, wherein said sulfated hyaluronic acid has a molecular weight of 40 kDa or more.

4. The method according to claim 2, wherein said sulfated hyaluronic acid has a molecular weight of 1300 kDa or more.

5. The method according to claim 3, wherein the amount of sulfation is about 50 to 60%.

6. The method according to claim 4, wherein the amount of sulfation is about 50 to 60%.

7. The anti-inflammatory agent according to claim 1, wherein said sulfated hyaluronic acid has a molecular weight of 40 kDa or more.

8. The anti-inflammatory agent according to claim 1, wherein said sulfated hyaluronic acid has a molecular weight of 1300 kDa or more.

9. The anti-inflammatory agent according to claim 7, wherein the amount of sulfation is about 50 to 60%.

10. The anti-inflammatory agent according to claim 8, wherein the amount of sulfation is about 50 to 60%.

* * * * *